United States Patent
Kim et al.

(10) Patent No.: US 12,359,235 B2
(45) Date of Patent: Jul. 15, 2025

(54) METHOD FOR PRODUCING BRANCHED DEXTRIN WITH IMPROVED WHITE TURBIDITY

(71) Applicant: DAESANG CORPORATION, Seoul (KR)

(72) Inventors: Min Su Kim, Icheon-si (KR); Ju Yeol Lee, Icheon-si (KR); Han Joong Ryu, Icheon-si (KR); Kyoung Ok Park, Icheon-si (KR); Hak Jun Kim, Icheon-si (KR)

(73) Assignee: DAESANG CORPORATION, Seoul (KR)

( * ) Notice: Subject to any disclaimer, the term of this patent is extended or adjusted under 35 U.S.C. 154(b) by 8 days.

(21) Appl. No.: 17/791,412

(22) PCT Filed: Oct. 1, 2021

(86) PCT No.: PCT/KR2021/013513
§ 371 (c)(1),
(2) Date: Jul. 7, 2022

(87) PCT Pub. No.: WO2022/169057
PCT Pub. Date: Aug. 11, 2022

(65) Prior Publication Data
US 2024/0200111 A1 Jun. 20, 2024

(30) Foreign Application Priority Data
Feb. 5, 2021 (KR) .......................... 10-2021-0016662

(51) Int. Cl.
*C12P 19/14* (2006.01)
*C12P 19/04* (2006.01)
*C12P 19/18* (2006.01)

(52) U.S. Cl.
CPC .............. *C12P 19/14* (2013.01); *C12P 19/04* (2013.01); *C12P 19/18* (2013.01)

(58) Field of Classification Search
CPC ........... C12P 19/14; C12P 19/04; C12P 19/18; C12P 19/22; C08B 30/18
See application file for complete search history.

(56) References Cited

U.S. PATENT DOCUMENTS

| 3,663,369 A | * | 5/1972 | Morehouse | ............. C12P 19/14 |
| | | | | 435/99 |
| 4,284,722 A | | 8/1981 | Tamuri et al. | |
| 8,445,460 B2 | * | 5/2013 | Deremaux | ........... A61K 31/195 |
| | | | | 536/124 |
| 2019/0352686 A1 | | 11/2019 | Li et al. | |

FOREIGN PATENT DOCUMENTS

| CN | 108841896 A | | 11/2018 | |
| JP | 2008-517599 A | | 5/2008 | |
| JP | 2011-130696 A | * | 7/2011 | .............. C12P 19/14 |
| JP | 2014-080518 A | * | 5/2014 | .............. C08B 30/18 |
| KR | 10-2010-0124323 A | | 11/2010 | |
| WO | WO 2019/153611 | * | 6/2019 | .............. C12P 19/04 |

OTHER PUBLICATIONS

Takata et al., Properties of Branching Enzyme from Hyperthermophilic Bacterium, Aquifex aeolicus, and Its Potential for Production of Highly-branched Cyclic Dextrin. J. Appl. Glycosci., 2003, vol. 50: 15-20. (Year: 2003).*
International Search Report of PCT/KR2021/013513 dated Jan. 13, 2022 [PCT/ISA/210].

* cited by examiner

*Primary Examiner* — Ganapathirama Raghu
(74) *Attorney, Agent, or Firm* — Sughrue Mion, PLLC

(57) ABSTRACT

Provided is a method for producing branched dextrin, the method comprising steps of: adding heat-resistant alpha-amylase to a starch suspension, heating the mixture at 85° C. to 115° C. to perform a liquefaction reaction, immediately heating the mixture at 125° C. to 145° C. to inactivate the heat-resistant alpha-amylase, and obtaining a liquefied starch solution including liquefied starch having a dextrose equivalent (DE) value of 2 to 10, and adding a branching enzyme to the liquefied starch solution in an amount of 0.6% (w/w) or more based on the dry weight of starch, proceeding with a branching reaction for 20 hour or more to generate branched dextrin, and then obtaining a solution with branched dextrin comprising branched dextrin having a dextrose equivalent (DE) value of 2 to 10 which stably controls the dextrose equivalent (DE) value of branched dextrin, and significantly suppresses the white turbidity that occurs during refrigeration.

2 Claims, 4 Drawing Sheets

FIG.2

| SAMPLE / TIME | Control (DE 11) | PREPARATION EXAMPLE 1 (ADDED AMOUNT OF BRANCHING ENZYME 0.2%) | PREPARATION EXAMPLE 2 (ADDED AMOUNT OF BRANCHING ENZYME 0.4%) | PREPARATION EXAMPLE 3 (ADDED AMOUNT OF BRANCHING ENZYME 0.8%) | PREPARATION EXAMPLE 4 (ADDED AMOUNT OF BRANCHING ENZYME 1.2%) |
|---|---|---|---|---|---|
| 0 DAY | | | | | |
| 7 DAY | | | | | |

FIG.3

| SAMPLE \ TIME | Control (DE 11) | PREPARATION EXAMPLE 5 (DE 4) | PREPARATION EXAMPLE 6 (DE 6) | PREPARATION EXAMPLE 7 (DE 8) | PREPARATION EXAMPLE 8 (DE 10) |
|---|---|---|---|---|---|
| 0 DAY | | | | | |
| 7 DAY | | | | | |

METHOD FOR PRODUCING BRANCHED DEXTRIN WITH IMPROVED WHITE TURBIDITY

CROSS REFERENCE TO RELATED APPLICATIONS

This application is a National Stage of International Application No. PCT/KR2021/013513 filed on Oct. 1, 2021, claiming priority based on Korean Patent Application No. 10-2021-0016662 filed on Feb. 5, 2021, the entire disclosures of which are incorporated herein by reference.

TECHNICAL FIELD

The present invention relates to a method for preparing branched dextrin, and more particularly, to a method for preparing branched dextrin that has a low dextrose equivalent (DE) value and hardly causes white turbidity during refrigeration at the same time.

BACKGROUND ART

Dextrin is a result produced by hydrolysis of starch with acid, heat, or enzymes and is a generic term for polysaccharides having a smaller molecular weight than starch. In general, dextrin is prepared by hydrolyzing starch with amylase and is a mixture of polymers in which the glucose unit structure is linked by α-1,4-glycosidic bonds or α-1,6-glycosidic bonds and has a dextrose equivalent (DE) value in the range of about 1 to 13.

In general, dextrin is partially water-soluble or completely water-soluble, and when an aqueous solution of dextrin having a dextrose equivalent (DE) value of about 10 or less is stored for a long time under refrigeration conditions, white turbidity occurs. In order to solve this problem, a method of increasing the dextrose equivalent (DE) value by additionally saccharifying the primarily prepared dextrin was proposed. For example, Korean Patent No. 10-1700826 discloses a method for producing a branched dextrin having a DE value of about 10 to 52 by simultaneously adding and enzymatically reacting beta-amylase and trans glucosidase to dextrin having a DE of about 8 or by simultaneously adding and enzymatically reacting maltose-producing amylase and transglucosidase to dextrin having a DE of about 8. The branched dextrin prepared in the prior art has a problem in that its use is limited because the DE value is too high.

DISCLOSURE

Technical Problem

The present invention has been derived from the conventional technical background, and an object of the present invention is to provide a method for preparing branched dextrin that has a low dextrose equivalent (DE) value and hardly causes white turbidity during refrigeration at the same time.

Technical Solution

The present inventors completed the present invention by finding that when preparing a liquefied starch solution, starch is hydrolyzed by treating with heat-resistant alpha-amylase and then heated to a high temperature instead of adjusting the pH for inactivation of heat-resistant alpha-amylase to maintain the dextrose equivalent (DE) value of liquified starch contained in liquefied starch solution at a constant level, and when the liquefied starch is treated with a branching enzyme to proceed with the branching reaction, the branched dextrin with improved white turbidity is produced with little change in dextrose equivalent (DE) value.

In order to achieve the object, an example of the present invention provides a method for producing branched dextrin, the method comprising steps of: adding heat-resistant alpha-amylase to a starch suspension, heating the mixture at 85° C. to 115° C. to perform a liquefaction reaction, immediately heating the mixture at 125° C. to 145° C. to inactivate the heat-resistant alpha-amylase, and obtaining a liquefied starch solution including liquefied starch having a dextrose equivalent (DE) value of 2 to 10, and adding a branching enzyme to the liquefied starch solution in an amount of 0.6% (w/w) or more based on the dry weight of starch, proceeding with a branching reaction for 20 hours or more to generate branched dextrin, and then obtaining the branched dextrin-containing solution comprising branched dextrin having a dextrose equivalent (DE) value of 2 to 10. The method for producing branched dextrin according to an embodiment of the present invention may preferably further comprise, after obtaining the branched dextrin-containing solution, steps of sequentially filtering, decolorizing, and ion exchange purifying the solution with branched dextrin to obtain a purified branched dextrin-containing solution.

In the method for producing branched dextrin according to an embodiment of the present invention, the type of starch constituting the starch suspension is not particularly limited, and for example, may include one selected from corn starch, waxy corn starch, potato starch, sweet potato starch, wheat starch, rice starch, tapioca starch, sago starch, sorghum starch or high amylose starch, and corn starch is preferable in consideration of the degree of improvement in white turbidity and economic feasibility. In addition, the starch concentration of the starch suspension is not particularly limited, and in consideration of the uniform mixing of heat-resistant alpha-amylase, its concentration is preferably 20 to 45% by weight, and preferably 25 to 40% by weight. The pH of the starch suspension is preferably adjusted to the optimum range for the enzyme for smooth hydrolysis before the heat-resistant alpha-amylase is added. For example, the pH of the starch suspension may be adjusted in the range of about 5 to 7, preferably in the range of 5.5 to 6.5. In addition, the starch suspension may include metal ions as co-catalysts to enhance the hydrolytic activity of heat-resistant alpha-amylase. For example, the starch suspension may include a divalent metal cation such as magnesium ion or calcium ion, preferably calcium ion as co-catalysts of heat-resistant alpha-amylase.

In the method for producing branched dextrin according to an embodiment of the present invention, heat-resistant alpha-amylase is added to the starch suspension, and the mixture is heat-treated to the optimum temperature range for the enzyme so that the liquefaction reaction proceeds. By the liquefaction reaction, 1,4-α-glycosidic bonds of starch are randomly hydrolyzed by heat-resistant alpha-amylase. The amount of heat-resistant alpha-amylase added for the liquefaction reaction of starch is not particularly limited, but preferably 0.01 to 0.1% (w/w) and preferably 0.02 to 0.08% (w/w) based on the dry weight of starch in order to easily control the dextrose equivalent (DE) value of the liquefied starch. Further, in the viewpoint of easily controlling the dextrose equivalent (DE) value of the liquefied starch, the liquefaction reaction may preferably consist of the first-step liquefaction reaction to add the heat-resistant alpha-amylase to the starch suspension followed by heat treatment at 100°

C. to 115° C. for 2 to 10 minutes, and the second-step liquefaction reaction to cool the resultant followed by heat treatment at 85° C. to 100° C. for 1 to 60 minutes. In addition, the liquefaction reaction may more preferably consist of the first-step liquefaction reaction to add the heat-resistant alpha-amylase to the starch suspension followed by heat treatment at 102° C. to 110° C. for 3 to 8 minutes, and the second-step liquefaction reaction to cool the resultant followed by heat treatment at 90° C. to 99° C. for 5 to 50 minutes. In the first-step liquefaction reaction, starch is rapidly hydrolyzed to economically obtain liquefied starch having a certain level of dextrose equivalent (DE) value, and in the second-step liquefaction reaction, starch is slowly hydrolyzed to easily adjust the dextrose equivalent (DE) value of the liquefied starch. In addition, after the starch liquefaction reaction is completed, heat-resistant alpha-amylase present in the liquefied starch solution is immediately inactivated to prevent an additional hydrolysis reaction from changing the dextrose equivalent (DE) value. In the method for producing branched dextrin according to an embodiment of the present invention, the inactivation of heat-resistant alpha-amylase is performed by a method of heating the liquefied starch solution at a high temperature, not the conventional method of adjusting the pH of the liquefied starch solution. When heat-resistant alpha-amylase is heat-treated at high temperatures, heat-resistant alpha-amylase has not been additionally hydrolyzed in the branching reaction described below to stably maintain the dextrose equivalent (DE) value of branched dextrin. The heat treatment temperature for inactivation of the heat-resistant alpha-amylase is preferably 127° C. to 140° C. in consideration of economic feasibility and suppression of thermal decomposition of liquefied starch. In addition, the heat treatment time for inactivation of the heat-resistant alpha-amylase is preferably 2 to 10 minutes, more preferably 3 to 8 minutes. In the method for producing branched dextrin according to an example embodiment of the present invention, the starch suspension is hydrolyzed with heat-resistant alpha-amylase to liquefy, and heat-resistant alpha-amylase is heat-treated at a high temperature to obtain a liquefied starch solution. The liquefied starch solution includes liquefied starch having a certain dextrose equivalent (DE) value, and the dextrose equivalent (DE) value of the liquefied starch is preferably 3 to 9 in consideration of inhibiting the occurrence of white turbidity of branched dextrin. In the present invention, the dextrose equivalent (DE) value of the liquefied starch contained in the liquefied starch solution is an average value contributed by liquefied starch having various sizes.

In the method for producing branched dextrin according to an embodiment of the present invention, when a branching enzyme is added to the liquefied starch followed by treatment in the optimum enzyme temperature range, a branching reaction proceeds. The α-1,4-glycosidic bond present in the liquefied starch is broken by the branching reaction, and α-1,6 branching is generated within the linear α-1,4 moiety. The pH of the liquefied starch is preferably adjusted to an optimal enzyme range for a smooth branching reaction before the branching enzyme is added thereto. For example, the pH of the liquefied starch solution may be adjusted in the range of about 5 to 7, preferably in the range of 5.5 to 6.5. The added amount of the branching enzyme is preferably 0.7 to 1.5% (w/w) based on the dry weight of the starch in consideration of the inhibition of the occurrence of white turbidity of the branched dextrin. In addition, the branching reaction temperature may be selected from a variety of ranges depending on the type of the branching enzyme used, for example, may be selected from 50° C. to 80° C., preferably 55° C. to 75° C. In addition, the branching reaction time is preferably 22 to 48 hours from the viewpoint of constantly maintaining the dextrose equivalent (DE) value of the branched dextrin generated in the branching reaction. In the method for producing branched dextrin according to an embodiment of the present invention, the branched dextrin-containing solution obtained after adding a branching enzyme to the liquefied starch solution to proceed with the branching reaction includes branched dextrin having a certain dextrose equivalent (DE) value, and the dextrose equivalent (DE) value of the branched dextrin is preferably 3 to 9 in consideration of inhibiting the occurrence of white turbidity of branched dextrin. In the present invention, the dextrose equivalent (DE) value of the branched dextrin contained in the branched dextrin-containing solution is an average value contributed by branched dextrin having various sizes.

The branched dextrin contained in the branched dextrin-containing solution obtained by the production method of the present invention is preferably mostly highly branched cyclic dextrin (HBCD). Corn starch is composed of about 20 to 30% (w/w) amylose and 70 to 80% (w/w) amylopectin. In particular, a hydrolysate of amylopectin is easily converted into highly branched cyclic dextrin (HBCD) by a branching reaction. The highly branched cyclic dextrin refers to a glucan having an inner branched cyclic structural portion and an outer branched structural portion and having a polymerization degree in the range of 20 to 10000. Here, the inner branched cyclic structural portion refers to a cyclic structural portion formed by an α-1,4-glucosidic bond and an α-1,6-glucosidic bond. The outer branched structural portion refers to a non-cyclic structural portion bonded to an inner branched cyclic structural portion. The highly branched cyclic dextrin has a significantly large degree of polymerization (molecular weight) and is a substance different from general cyclodextrin in which 6 to 8 glucoses are bonded, such as α-cyclodextrin (n=6), β-cyclodextrin (n=7), and γ-cyclodextrin (n=8). Highly branched cyclic dextrin has an overall helical structure, whereas cyclodextrin has an overall cyclic structure. In highly branched cyclic dextrin, the chain of highly branched glucose polymer polysaccharides (e.g., amylopectin) is broken through alpha-1,6 bonds to the linear chain, and this broken linkage has a cyclic chain by a branching enzyme. The branching enzyme is a glucan chain transferase widely distributed in animals, plants, and microorganisms and acts on the seam portion of the cluster structure of amylopectin to catalyze a reaction to cycle it. Specific examples of the highly branched cyclic dextrin include glucan having an inner branched cyclic structural portion and an outer branched structural portion described in Japanese Patent Laid-Open No. 8-134104. In addition, as a commercial product of highly branched cyclic dextrin, Cluster Dextrin® is supplied by Ezaki Glico of Japan.

Advantageous Effects

When branched dextrin is prepared using the method according to the present invention, it is possible to stably control the dextrose equivalent (DE) value of branched dextrin, and furthermore, it is possible to significantly inhibit the white turbidity that occurs during refrigeration. In addition, when branched dextrin is prepared using the method according to the present invention, there is an advantage in that unliquefied starch is completely liquefied in the process of inactivating alpha-amylase present in the liquefied starch solution by heat treatment at a high temperature, and a separate hydrochloric acid or the like is not used to inactivate alpha-amylase, thereby reducing the load of the ion exchange purification used to purify the branched dextrin.

DESCRIPTION OF DRAWINGS

FIG. 2 is a view showing the results of measuring the level of white turbidity of the branched dextrin obtained by preparing branched dextrin by varying the adding amount of branching enzyme in Example 3 of the present invention (Preparation Examples 1 to 4).

FIG. 3 is a view showing the results of measuring the level of white turbidity of the branched dextrin obtained by preparing branched dextrin having different dextrose equivalent (DE) values in Example 4 of the present invention (Preparation Examples 5 to 8).

DETAILED DESCRIPTION OF EMBODIMENT

Figure 1:
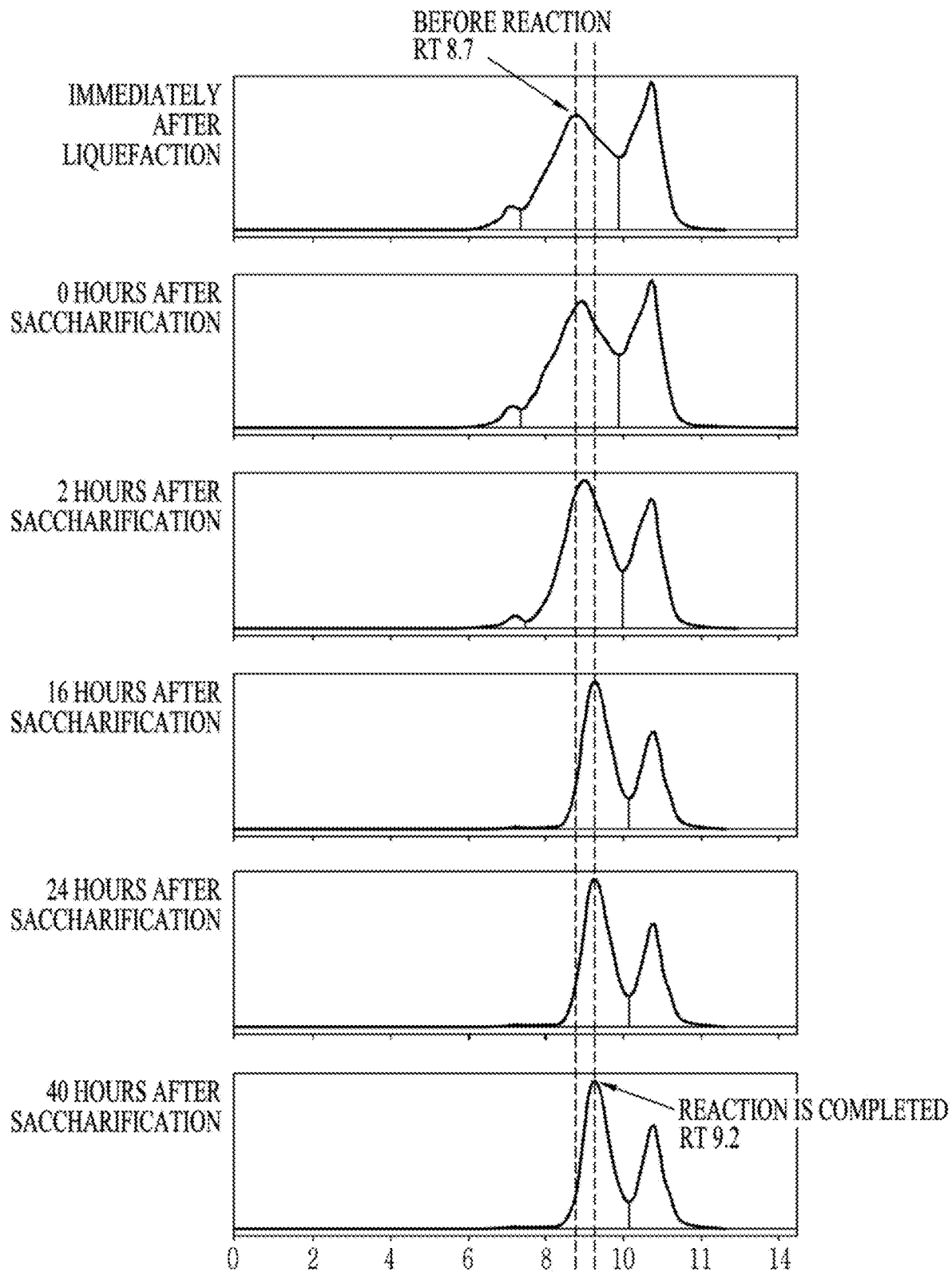
FIG. 1 is a view showing the results of HPLC analysis of the molecular weight of the reaction product according to the lapse of a branching reaction time in Example 2 of the present invention.

Hereinafter, the present invention will be described in detail through examples. However, the following examples are only for clearly illustrating the technical features of the present invention and do not limit the protection scope of the present invention.

Example 1: Establishment of Manufacturing Conditions for Liquefied Starch Solution Through Two-Step Liquefaction Corn starch was suspended in ion exchanged water to prepare a starch suspension having a starch concentration of 30% by weight. Thereafter, the pH of the starch suspension was adjusted to about 5.9, and heat-resistant alpha-amylase (product name: SEBstar HTL; supplier: Advanced Enzymes) was added thereto in an amount of 0.04% (w/w) based on the dry weight of the starch. Calcium chloride was added so that the concentration of calcium ions was about 85 ppm, and then the mixture was heat-treated at about 105° C. for about 5 minutes to proceed with the first-step liquefaction reaction. The dextrose equivalent (DE) value of the first-step treated liquefied starch solution obtained by the first-step liquefaction reaction was about 4. Thereafter, the first-step treated liquefied starch solution was cooled to about 95° C. and left at about 95° C. for about 20 minutes to proceed with the second-step liquefaction reaction. Thereafter, the enzyme inactivation was carried out by heat-treating the second-step treated liquefied starch solution at about 130° C. for about 5 minutes. The dextrose equivalent (DE) value of the second-step treated liquefied starch solution obtained after enzyme inactivation was about 6.5. The second-step treated liquefied starch solution obtained after the enzyme inactivation was cooled to about 90° C. While the solution was left at about 90° C. and the freezing point of the second-step treated liquefied starch solution was measured according to the settling time, and the results are summarized in Table 1 below.

TABLE 1

| Settling time (minutes) | 0 | 30 | 60 | 90 | 120 |
|---|---|---|---|---|---|
| Freezing point (° C.) | 75 | 75 | 75 | 75 | 75 |

As shown in Table 1 above, it was confirmed that the heat-resistant alpha-amylase was completely inactivated in the second-step treated liquefied starch solution, and there was no change in the freezing point even after a settling time elapsed.

Example 2: Establishment of Branching Reaction Conditions for Second-Step Treated Liquefied Starch Solution Using Branching Enzyme The pH of the second-step treated liquefied starch solution obtained in Example 1 was adjusted to about 6.0. A branching enzyme (product name: Branchzyme; supplier: Novozymes) was added in an amount of 1% (w/w) based on the dry weight of the raw starch. A branching reaction was performed at 70° C. to produce branched dextrin. The branching enzyme (EC number: 2.4.1.18) is an enzyme that transfers a portion of an α-1,4-D-glucan chain to a free 6-hydroxyl group of the same glucan chain or a free 6-hydroxyl group of an adjacent glucan chain to produce α-1,6-glucosidic bonds and consequently increase the number of branch points. It is also called 1,4-α-glucan branching enzyme, Q-enzyme, branching glycosyltransferase or glycogen branching enzyme. The branching reaction is a reaction induced by a branching enzyme and a reaction in which α-1,4-glycosidic bonds present in starch or liquid starch are broken and α-1,6 branches are generated within the linear α-1,4 portion.

[Schematic Diagram of Branching Reaction Using Amylose-Type Liquefied Starch as a Substrate]

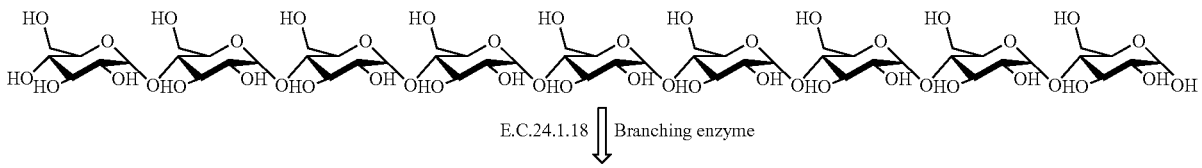

-continued

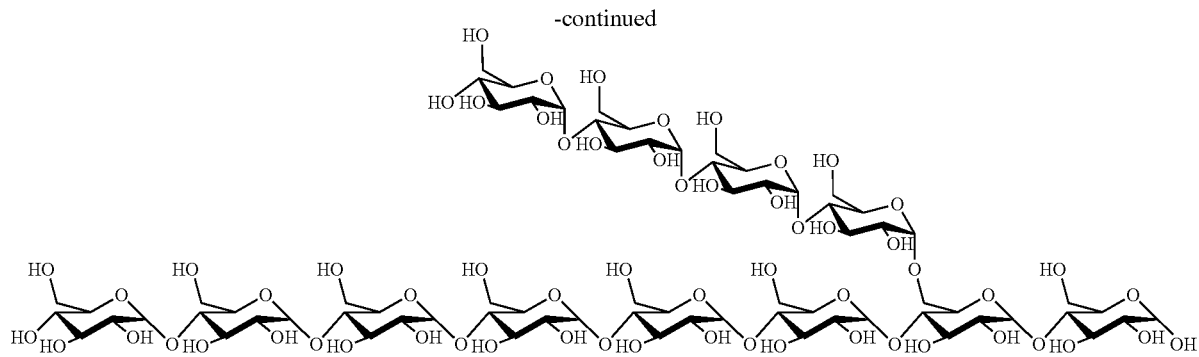

The reaction product was sampled for each branching reaction time, and the sample was prepared through a series of processes such as filtration, decolorization and ion exchange purification. The molecular weight of the sampled sample was determined using HPLC. HPLC analysis conditions are as follows.

Column: SB-806M HQ column
Mobile phase solvent: water or 0.1N sodium nitrate
Flow rate: 1 ml/min
Column temperature: 40° C.
Passing time: 20 min FIG. 1 is a view showing the results of HPLC analysis of the molecular weight of the reaction product according to the lapse of a branching reaction time in Example 2 of the present invention. In FIG. 1, the term "saccharification" refers to a branching reaction. As shown in FIG. 1, the retention time of the liquefied starch contained in the second-step liquefied starch solution obtained in Example 1 was about 8.7 minutes, and as the branching reaction time elapsed, the retention time of the reaction product increased, but when the branching reaction time was 24 hours or more, the retention time of the reaction product was constant at about 9.2 minutes. From the above results, it may be seen that when the branching reaction time is 24 hours, the branching reaction is completed and does not proceed any further. Meanwhile, when the branching reaction time was 24 hours or more, the dextrose equivalent (DE) value of the prepared branched dextrin was almost the same as that of the second-step treated liquefied starch solution (liquefied starch) used as a substrate without any significant difference.

Example 3: Measurement of White Turbidity Level of Branched Dextrin According to the Adding Amount of Branching Enzyme (1) Preparation of Branched Dextrin Preparation Example 1

The pH of the second-step treated liquefied starch solution obtained in Example 1 was adjusted to about 6.0. The branching enzyme (product name: Branchzyme; supplier: Novozymes) was added in an amount of 0.2% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution.

Preparation Example 2

The pH of the second-step treated liquefied starch solution obtained in Example 1 was adjusted to about 6.0. The branching enzyme (product name: Branchzyme; supplier: Novozymes) was added in an amount of 0.4% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution.

Preparation Example 3

The pH of the second-step treated liquefied starch solution obtained in Example 1 was adjusted to about 6.0. The branching enzyme (product name: Branchzyme; supplier: Novozymes) was added in an amount of 0.8% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution.

Preparation Example 4

The pH of the second-step treated liquefied starch solution obtained in Example 1 was adjusted to about 6.0. The branching enzyme (product name: Branchzyme; supplier: Novozymes) was added in an amount of 1.2% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution.

(2) Measurement of White Turbidity Level of Branched Dextrin

While the branched dextrin-containing solutions obtained in Preparation Examples 1 to 4 were stored under refrigerated conditions (4° C.) for 7 days, the occurrence of white turbidity was visually observed.

FIG. 2 is a view showing the results of measuring the level of white turbidity of the branched dextrin obtained by preparing branched dextrin by varying the adding amount of branching enzyme in Example 3 of the present invention (Preparation Examples 1 to 4). In FIG. 2, sample "Control" is a commercially available dextrin product and has a dextrose equivalent (DE) value of about 11. The sample "Control" was a dextrin manufactured through a series of processes in which the pH of a suspension of corn starch having a concentration of about 30% (w/w) was adjusted to about 6.2, heat-resistant alpha-amylase (product name: KLEISTASE L-1; supplier: AMANO Enzymes) was added thereto in an amount of 0.08% (w/w) relative to the dry weight of the starch, liquefaction reaction was carried out at about 86° C., and the pH of the liquefied starch solution was adjusted to about 3 to inactivate the enzyme, followed by a series of processes such as filtration, decolorization and ion exchange purification. As shown in FIG. 2, when the branched dextrin was prepared by treating the second-step treated liquefied starch solution obtained in Example 1 with a branching enzyme, the adding amount of branching enzyme was 0.8% (w/w) or more compared to the dry weight of the raw starch used to prepare the liquefied starch solution, white turbidity of the branched dextrin did not occur. On the other hand, a commercially available dextrin product, "Control" had a significant level of white turbidity after about 7 days of refrigerated storage.

Example 4: Determination of White Turbidity Level of Branched Dextrin According to Dextrose Equivalent (DE) Value (1) Preparation of Branched Dextrin Preparation Example 5

Corn starch was suspended in ion exchanged water to prepare a starch suspension having a starch concentration of 30 wt %. Then, the pH of the starch suspension was adjusted to about 5.9. Heat-resistant alpha-amylase (product name: SEBstar HTL; supplier: Advanced Enzymes) was added thereto in an amount of 0.04% (w/w) based on the dry weight of the starch, and calcium chloride was added so that the concentration of calcium ions was about 85 ppm. The liquefaction reaction was carried out by heat treatment at about 105° C. for about 5 minutes. Thereafter, the enzyme inactivation was performed by heating the liquefied starch solution at about 130° C. for about 5 minutes. The dextrose equivalent (DE) value of the liquefied starch solution obtained after enzyme inactivation was about 4. Then, the pH of the liquefied starch solution was adjusted to about 6.0. The branching enzyme (product name: Branchzyme; supplier: Novozymes) was added in an amount of 0.8% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution. The obtained branched dextrin had a dextrose equivalent (DE) value of about 4.

Preparation Example 6

Corn starch was suspended in ion exchanged water to prepare a starch suspension having a starch concentration of 30 wt %. Then, the pH of the starch suspension was adjusted to about 5.9. Heat-resistant alpha-amylase (product name: SEBstar HTL; supplier: Advanced Enzymes) was added thereto in an amount of 0.04% (w/w) based on the dry weight of the starch, and calcium chloride was added so that the concentration of calcium ions was about 85 ppm. Thereafter, the first-step liquefaction reaction was performed by heating at about 105° C. for about 5 minutes. The dextrose equivalent (DE) value of the first-step treated liquefied starch solution obtained by the first-step liquefaction reaction was about 4. Then, the first-step treated liquefied starch solution was cooled to about 95° C. and left at about 95° C. for about 15 minutes to proceed with the second-step liquefaction reaction. Thereafter, the enzyme inactivation was carried out by heat-treating the second-step treated liquefied starch solution at about 130° C. for about 5 minutes. The dextrose equivalent (DE) value of the second-step treated liquefied starch solution obtained after enzyme inactivation was about 6. Then, the pH of the second-step treated liquefied starch solution was adjusted to about 6.0. The branching enzyme (product name: Branchzyme; supplier: Novozymes) was added in an amount of 0.8% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution. The obtained branched dextrin had a dextrose equivalent (DE) value of about 6.

Preparation Example 7

Except that the second-step liquefaction reaction was performed at about 95° C. for about 25 minutes to obtain a second-step treated liquefied starch solution having a dextrose equivalent (DE) value of about 8, a branched dextrin having a dextrose equivalent (DE) value of about 8 was prepared in the same conditions and methods as in Preparation Example 6.

Preparation Example 8

Except that the second-step liquefaction reaction was performed at about 95° C. for about 30 minutes to obtain a second-step treated liquefied starch solution having a dextrose equivalent (DE) value of about 10, a branched dextrin having a dextrose equivalent (DE) value of about 10 was prepared in the same conditions and methods as in Preparation Example 6.

(2) Measurement of White Turbidity Level of Branched Dextrin

While the branched dextrin-containing solutions obtained in Preparation Examples 5 to 8 were stored under refrigerated conditions (4° C.) for 7 days, the occurrence of white turbidity was visually observed.

FIG. 3 is a view showing the results of measuring the level of white turbidity of the branched dextrin obtained by preparing branched dextrin having different dextrose equivalent (DE) values in Example 4 of the present invention (Preparation Examples 5 to 8). In FIG. 3, the sample "Control" is a commercially available dextrin product, and the dextrose equivalent (DE) value is about 11, which is the same as that described in FIG. 2. In the process of preparing the liquefied starch solution as in Preparation Examples 5 to 8, instead of inactivating the heat-resistant alpha-amylase by adjusting the pH, inactivation is carried out by high-temperature heat treatment at about 130° C. to completely block the additional hydrolysis reaction and to stabilize the dextrose equivalent (DE) value of the liquefied starch solution. After that, when the liquefied starch solution is treated with a branching enzyme and the branching reaction is completed, branched dextrin may be prepared to have a dextrose equivalent (DE) value almost identical to that of the liquefied starch solution. As shown in FIG. 3, although the branched dextrin prepared in this way has a low dextrose equivalent (DE) value of 10 or less, white turbidity does not occur during long-term refrigeration. Meanwhile, the commercially available dextrin product "Control" showed a higher DE value compared to the branched dextrin prepared in Preparation Examples 5 to 8, but white turbidity occurred to a significant level after about 7 days of refrigeration.

Example 5: Measurement of White Turbidity Level of Dextrin According to the Preparation Method (1) Preparation of Dextrin Comparative Preparation Example 1

Corn starch was suspended in ion exchanged water to prepare a starch suspension having a starch concentration of 30 wt %. Then, the pH of the starch suspension was adjusted to about 5.9. Heat-resistant alpha-amylase (product name: SEBstar HTL; supplier: Advanced Enzymes) was added thereto in an amount of 0.04% (w/w) based on the dry weight of the starch, and calcium chloride was added so that the concentration of calcium ions was about 85 ppm. Thereafter, the first-step liquefaction reaction was performed by heating at about 105° C. for about 5 minutes. The dextrose equivalent (DE) value of the first-step treated liquefied starch solution obtained by the first-step liquefaction reaction was about 4. Then, the first-step treated liquefied starch solution was cooled to about 95° C. and left at about 95° C. for about 25 minutes to proceed with the second-step liquefaction reaction. Thereafter, the enzyme inactivation was carried out by heat-treating the second-step treated liquefied starch solution at about 130° C. for about 5 minutes. The dextrose equivalent (DE) value of the second-step treated liquefied starch solution obtained after enzyme inactivation was about 8. Thereafter, the second-step treated liquefied starch solution obtained after enzyme inactivation was treated by a series of processes such as filtration, decolorization and ion exchange purification to obtain a dextrin-containing solution. The obtained dextrin had a dextrose equivalent (DE) value of about 8.

Comparative Preparation Example 2

Corn starch was suspended in ion exchanged water to prepare a starch suspension having a starch concentration of 30 wt %. Then, the pH of the starch suspension was adjusted to about 5.9. Heat-resistant alpha-amylase (product name: SEBstar HTL; supplier: Advanced Enzymes) was added thereto in an amount of 0.04% (w/w) based on the dry weight of the starch, and calcium chloride was added so that the concentration of calcium ions was about 85 ppm. Thereafter, the first-step liquefaction reaction was performed by heating at about 105° C. for about 5 minutes. The dextrose equivalent (DE) value of the first-step treated liquefied starch solution obtained by the first-step liquefaction reaction was about 4. Then, the first-step treated liquefied starch solution was cooled to about 95° C. and left at about 95° C. for about 20 minutes to proceed with the second-step liquefaction reaction. Then, the pH of the second-step treated liquefied starch solution was adjusted to about 3. Thereafter, the enzyme inactivation was carried out by heating at about 100° C. The pH of the second-step treated liquefied starch solution after the enzyme inactivation was adjusted to about 6.0. The branching enzyme (product name: Branchzyme; supplier: Novozymes) was added in an amount of 0.8% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution. In the ion exchange purification process, about twice the load was applied compared to Preparation Example 7. The obtained branched dextrin had a dextrose equivalent (DE) value of about 8.

Comparative Preparation Example 3

Corn starch was suspended in ion exchanged water to prepare a starch suspension having a starch concentration of 30 wt %. Then, the pH of the starch suspension was adjusted to about 5.9. Heat-resistant alpha-amylase (product name: SEBstar HTL; supplier: Advanced Enzymes) was added thereto in an amount of 0.04% (w/w) based on the dry weight of the starch, and calcium chloride was added so that the concentration of calcium ions was about 85 ppm. Thereafter, the first-step liquefaction reaction was performed by heating at about 105° C. for about 5 minutes. The dextrose equivalent (DE) value of the first-step treated liquefied starch solution obtained by the first-step liquefaction reaction was about 4. Then, the first-step treated liquefied starch solution was cooled to about 95° C. and left at about 95° C. for about 15 minutes to proceed with the second-step liquefaction reaction. Then, the pH of the second-step treated liquefied starch solution was adjusted to about 6.0. The branching enzyme (product name: Branchzyme; supplier: Novozymes) was added in an amount of 0.8% (w/w) based on the dry weight of the raw starch. A branching reaction was performed at 70° C. for about 24 hours to produce branched dextrin. Thereafter, the solution containing the branching reaction product was treated by a series of processes such as filtration, decolorization and ion exchange purification to obtain a branched dextrin-containing solution. The obtained branched dextrin had a dextrose equivalent (DE) value of about 8.

(2) Determination of the White Turbidity Level of Dextrin

While the dextrin-containing solutions obtained in Preparation Example 7 and Comparative Preparation Examples 1 to 3 were stored under refrigerated conditions (4° C.) for 7 days, the occurrence of white turbidity was visually observed.

Figure 4:
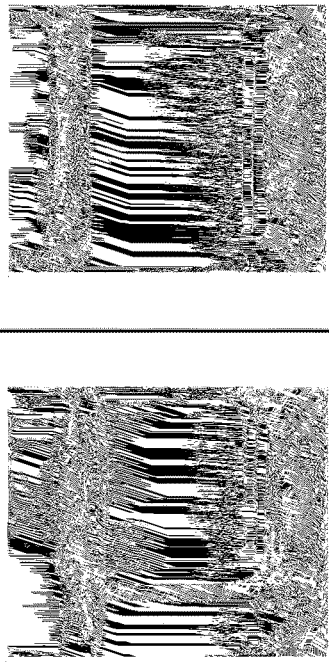
FIG. 4 is a view showing the results of measuring the level of white turbidity of the dextrin obtained by preparing dextrin having a dextrose equivalent (DE) value of about 8 by changing the preparation method in Example 5 of the present invention (Preparation Example 7, Comparative Preparation Example 1 to Comparative Preparation Example 3).

FIG. 4 is a view showing the results of measuring the level of white turbidity of the dextrin obtained by preparing dextrin having a dextrose equivalent (DE) value of about 8 by changing the preparation method in Example 5 of the present invention (Preparation Example 7, Comparative Preparation Example 1 to Comparative Preparation Example 3). As shown in FIG. 4, in the case of the branched dextrin-containing solution prepared in Preparation Example 7, white turbidity did not occur even when stored for 7 days under refrigerated conditions, whereas the dextrin-containing solution prepared in Comparative Preparation Examples 1 to 3, white turbidity occurred at a significant level when stored for 7 days under refrigerated conditions.

As described above, the present invention has been described through the above embodiments, but the present invention is not necessarily limited thereto, and various modifications are possible without departing from the scope and spirit of the present invention. Accordingly, the protection scope of the present invention should be construed to include all embodiments falling within the scope of the claims appended hereto.

The invention claimed is:

1. A method for producing branched dextrin, the method comprising steps of:

adding heat-resistant alpha-amylase to a starch suspension, heating the mixture to perform a liquefaction reaction, immediately heating the mixture at 127° C. to 140° C. to inactivate the heat-resistant alpha-amylase, and obtaining a liquefied starch solution including liquefied starch having a dextrose equivalent (DE) value of 4 to 8, and adding a branching enzyme to the liquefied starch solution in an amount of 0.7 to 1.5% (w/w) based on the dry weight of starch, proceeding with a branching reaction for 22 hours to 48 hours to generate branched dextrin, and then obtaining a solution with branched dextrin comprising branched dextrin having a dextrose equivalent (DE) value of 4 to 8, wherein the starch is corn starch, wherein the starch concentration of the starch suspension is 25 to 40% by weight, wherein the pH of the starch suspension is 5.5 to 6.5, wherein the starch suspension includes calcium ion as co-catalyst of heat-resistant alpha-amylase, wherein the added amount of the heat-resistant alpha-amylase is 0.02 to 0.08% (w/w) based on the dry weight of the starch, wherein the liquefaction reaction consists of the first-step liquefaction reaction to add the heat-resistant alpha-amylase to the starch suspension followed by heat treatment at 102° C. to 110° C. for 3 to 8 minutes, and the second-step liquefaction reaction to cool the resultant followed by heat treatment at 90° C. to 99° C. for 5 to 50 minutes, wherein the pH of the liquefied starch solution is adjusted in the range of 5.5 to 6.5, and wherein the branching reaction temperature is selected from 55° C. to 75° C.

2. The method of claim 1, wherein the branched dextrin is highly branched cyclic dextrin (HBCD).

* * * * *